US006468538B1

United States Patent
Rodriguez Garcia et al.

(10) Patent No.: US 6,468,538 B1
(45) Date of Patent: Oct. 22, 2002

(54) RECOMBINANT PROTEINS FOR THE FUSION OF THE PORCINE REPRODUCTIVE AND RESPIRATORY SYNDROME VIRUS AND ITS USE IN DIAGNOSIS

(75) Inventors: Maria Jose Rodriguez Garcia; Antonio Sanz Fernandez; Jose Ignacio Casal Alvarez, all of Madrid (ES)

(73) Assignee: Inmunologia Y Genetica Aplicada, S.A., Madrid (ES)

( * ) Notice: Subject to any disclaimer, the term of this patent is extended or adjusted under 35 U.S.C. 154(b) by 0 days.

(21) Appl. No.: 09/331,924

(22) PCT Filed: Dec. 24, 1997

(86) PCT No.: PCT/ES97/00313

§ 371 (c)(1),
(2), (4) Date: Jun. 29, 1999

(87) PCT Pub. No.: WO98/29550

PCT Pub. Date: Jul. 9, 1998

(30) Foreign Application Priority Data

Dec. 30, 1996 (ES) .............................. P 9602770

(51) Int. Cl.[7] ...................... A61K 39/12; A61K 39/295
(52) U.S. Cl. .............................. 424/186.1; 424/201.1; 424/198.1; 424/204.1; 530/350; 536/23.72
(58) Field of Search ........................... 424/186.1, 201.1, 424/198.1, 204.1; 530/350; 536/23.72

(56) References Cited

FOREIGN PATENT DOCUMENTS

EP          0717108 A      6/1996

OTHER PUBLICATIONS

Witzgall et al. Analytical Biochemistry, 1994, 223, pp. 291–298, 1994.*

Mounir, S. et al."Identification and characterization of the porcine reproductive and respiratory virus ORFS 7,5 and 4 products". Advances in Experimental Medicine and Biology. 1995. vol. 380. pp. 317–320.

Mardassi, H.et al. "Identification of major differences in the nucleocapsid protein genes of a Quebec strain and European strains of porcine reproductive and respiratory syndrome virus". Journal of General Virology. 1994. vol. 75. pp. 681–685.

Studier, FW. et al. "Use of T7 RNA polymerase to direct expression of cloned genes". Methods in Enzymology. 1990. vol. 185. pp. 60–89.

Conzelmann, K–K.et al."Molecular characterization of Porcine Reproductive and Respiratory Syndrome Virus, a member of the Arterivirus Group". Virology. 1993. vol. 193. pp. 329–339.

Wieczorek–Krohmer, M.et al."Porcine reproductive and respiratory syndrome virus(PRRSV): Monoclonal antibodies detect comunan epitopes on two viral proteins of European and U.S.strains". Veterinary Microbiology. 1996. vol. 51. pp. 257–266.

Rodriguez, M.J. et al."Epitope mapping of the nucleo capsid protein of European and North American isolates or porcine reproductive and respiratory syndrome virus". Journal of General Virology. 1997. vol. 78. pp. 2269–2278.

* cited by examiner

Primary Examiner—Ali R. Salimi
(74) Attorney, Agent, or Firm—Harrison & Egbert

(57) ABSTRACT

The recombinant fusion proteins comprise the protein of the nucleocapsid of the porcine reproductive and respiratory syndrome virus (PRRSV), obtained both from a European isolate of PRRSV as well as from an American isolates, fused to a sequence of amino acids derived from the system chosen for the expression of said recombinant fusion protein, either directly or by means of a binding area formed by a small number of amino acids. These recombinant fusion proteins are suited for their use in the diagnosis of PRRSV.

3 Claims, No Drawings

SEQUENCE LISTING

```
<160> NUMBER OF SEQ ID NOS:  9

<210> SEQ ID NO 1
<211> LENGTH: 128
<212> TYPE: PRT
<213> ORGANISM: Porcine reproductive and respiratory syndrome virus

<400> SEQUENCE: 1
```

Met Ala Gly Lys Asn Gln Ser Gln Lys Lys Lys Ser Ala Ala Pro
1               5                   10                  15

Met Gly Asn Gly Gln Pro Val Asn Gln Leu Cys Gln Leu Leu Gly Ala
                20                  25                  30

Met Ile Lys Ser Gln Arg Gln Gln Pro Arg Gly Gly Gln Ala Lys Lys
            35                  40                  45

Lys Lys Pro Glu Lys Pro His Phe Pro Leu Ala Ala Glu Asp Asp Ile
    50                  55                  60

Arg His His Leu Thr Gln Thr Glu Arg Ser Leu Cys Leu Gln Ser Ile
65                  70                  75                  80

Gln Thr Ala Phe Asn Gln Gly Ala Gly Thr Ala Ser Leu Ser Ser Ser
                85                  90                  95

Gly Lys Val Ser Phe Gln Val Glu Phe Met Leu Pro Val Ala His Thr
            100                 105                 110

Val Arg Leu Ile Arg Val Thr Ser Thr Ser Ala Ser Gln Gly Ala Ser
        115                 120                 125

<210> SEQ ID NO 2
<211> LENGTH: 123
<212> TYPE: PRT
<213> ORGANISM: Porcine reproductive and respiratory syndrome virus

<400> SEQUENCE: 2

Met Pro Asn Asn Thr Gly Arg Gln Gln Lys Lys Lys Gly Asp Gly
1               5                   10                  15

Gln Pro Val Asn Gln Leu Cys Gln Met Leu Gly Lys Ile Ile Ala Gln
                20                  25                  30

Gln Asn Gln Ser Arg Gly Lys Gly Pro Gly Lys Lys Asn Lys Lys Lys
            35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Ala Val Glu Phe Ser Leu Pro Thr His His Thr Val
            100                 105                 110

Arg Leu Ile Arg Val Thr Ala Ser Pro Ser Ala
        115                 120

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: synthetic
      DNA; Original Source (Organism PRRSV, Strain  Europea, Isolated
      Toledo 4/96)

<400> SEQUENCE: 3
cctcgtcaag tatggccggt a                                        21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: synthetic
      DNA; Original Source (Organism PRRSV, Strain  Europea, Isolated
      Toledo 4/96)

<400> SEQUENCE: 4
gactgtcaaa ttagcttgca ccc                                           23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: synthetic
      DNA; Original Source (Organism PRRSV, Strain Americana, Isolated
      Canada 14/96)

<400> SEQUENCE: 5
taaatatgcc aaataacacc g                                             21

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: synthetic
      DNA; Original Source (Organism PRRSV, Strain Americana, Isolated
      Canada 14/96)

<400> SEQUENCE: 6
ccatcatgag ggtgatcc                                                 18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
ctatccgcaa cgttatgggc                                               20

<210> SEQ ID NO 8
<211> LENGTH: 393
<212> TYPE: PRT
<213> ORGANISM: Porcine reproductive and respiratory syndrome virus

<400> SEQUENCE: 8

Met Ala Ser Met Thr Gly Gly Gln Gln Met Gly Thr Asn Gln Gln Lys
 1               5                  10                  15

Gly Val Val Ala Ala Gly Asp Lys Leu Ala Leu Phe Leu Lys Val Phe
            20                  25                  30

Gly Gly Glu Val Leu Thr Ala Phe Ala Arg Thr Ser Val Thr Thr Ser
        35                  40                  45

Arg His Met Val Arg Ser Ile Ser Ser Gly Lys Ser Ala Gln Phe Pro
    50                  55                  60

Val Leu Gly Arg Thr Gln Ala Ala Tyr Leu Ala Pro Gly Glu Asn Leu
65                  70                  75                  80

Asp Asp Lys Arg Lys Asp Ile Lys His Thr Glu Lys Val Ile Thr Thr
                85                  90                  95

Asp Gly Leu Leu Thr Ala Asp Val Leu Ile Tyr Asp Ile Glu Asp Ala
            100                 105                 110

Met Asn His Tyr Asp Val Arg Ser Glu Tyr Thr Ser Gln Leu Gly Glu
        115                 120                 125

Ser Leu Ala Met Ala Ala Asp Gly Ala Val Leu Ala Glu Ile Ala Gly

-continued

```
            130                 135                 140
Leu Cys Asn Val Glu Ser Lys Tyr Asn Glu Asn Ile Glu Gly Leu Gly
145                 150                 155                 160

Thr Ala Thr Val Ile Gly Thr Thr Gln Asn Lys Ala Ala Leu Thr Asp
                165                 170                 175

Gln Val Ala Leu Gly Lys Glu Ile Ile Ala Ala Leu Thr Lys Ala Arg
            180                 185                 190

Ala Ala Leu Thr Lys Asn Tyr Val Pro Ala Ala Asp Arg Val Phe Tyr
        195                 200                 205

Cys Asp Pro Asp Ser Tyr Ser Ala Ile Leu Ala Ala Leu Met Pro Asn
    210                 215                 220

Ala Ala Asn Tyr Ala Ala Leu Ile Asp Pro Glu Lys Gly Ser Ile Arg
225                 230                 235                 240

Asn Val Met Gly Phe Glu Val Val Glu Val Pro His Leu Thr Ala Gly
                245                 250                 255

Gly Ala Gly Ser Pro Thr Ser Ser Met Ala Gly Lys Asn Gln Ser
                260                 265                 270

Gln Lys Lys Lys Lys Ser Ala Ala Pro Met Gly Asn Gly Gln Pro Val
            275                 280                 285

Asn Gln Leu Cys Gln Leu Leu Gly Ala Met Ile Lys Ser Gln Arg Gln
        290                 295                 300

Gln Pro Arg Gly Gly Gln Ala Lys Lys Lys Pro Glu Lys Pro His
305                 310                 315                 320

Phe Pro Leu Ala Ala Glu Asp Asp Ile Arg His His Leu Thr Gln Thr
                325                 330                 335

Glu Arg Ser Leu Cys Leu Gln Ser Ile Gln Thr Ala Phe Asn Gln Gly
            340                 345                 350

Ala Gly Thr Ala Ser Leu Ser Ser Ser Gly Lys Val Ser Phe Gln Val
        355                 360                 365

Glu Phe Met Leu Pro Val Ala His Thr Val Arg Leu Ile Arg Val Thr
    370                 375                 380

Ser Thr Ser Ala Ser Gln Gly Ala Ser
385                 390

<210> SEQ ID NO 9
<211> LENGTH: 386
<212> TYPE: PRT
<213> ORGANISM: Porcine reproductive and respiratory syndrome virus

<400> SEQUENCE: 9

Met Ala Ser Met Thr Gly Gly Gln Gln Met Gly Thr Asn Gln Gly Lys
1               5                   10                  15

Gly Val Val Ala Ala Gly Asp Lys Leu Ala Leu Phe Leu Lys Val Phe
            20                  25                  30

Gly Gly Glu Val Leu Thr Ala Phe Ala Arg Thr Ser Val Thr Thr Ser
        35                  40                  45

Arg His Met Val Arg Ala Ile Ser Ser Gly Lys Ser Ala Gln Phe Pro
    50                  55                  60

Val Leu Gly Arg Thr Gln Ala Ala Tyr Leu Ala Pro Gly Glu Asn Leu
65                  70                  75                  80

Asp Asp Lys Arg Lys Asp Ile Lys His Thr Glu Lys Val Ile Thr Ile
                85                  90                  95

Asp Gly Leu Leu Thr Ala Asp Val Leu Ile Tyr Asp Ile Glu Asp Ala
            100                 105                 110
```

```
Met Asn His Tyr Asp Val Arg Ser Glu Tyr Thr Ser Gln Leu Gly Glu
        115                 120                 125

Ser Leu Ala Met Ala Ala Asp Gly Ala Val Leu Ala Glu Ile Ala Gly
        130                 135                 140

Leu Cys Asn Val Glu Ser Lys Tyr Asn Glu Asn Ile Glu Gly Leu Gly
145                 150                 155                 160

Thr Ala Thr Val Ile Glu Thr Thr Gln Asn Lys Ala Ala Leu Thr Asp
                165                 170                 175

Gln Val Ala Leu Gly Lys Glu Ile Ile Ala Ala Leu Thr Lys Ala Arg
                180                 185                 190

Ala Ala Leu Thr Lys Asn Tyr Val Pro Ala Ala Asp Arg Val Phe Tyr
        195                 200                 205

Cys Asp Pro Asp Ser Tyr Ser Ala Ile Leu Ala Ala Leu Met Pro Asn
        210                 215                 220

Ala Ala Asn Tyr Ala Ala Leu Ile Asp Pro Glu Lys Gly Ser Ile Arg
225                 230                 235                 240

Asn Val Met Gly Phe Glu Val Val Glu Val Pro His Leu Thr Ala Gly
                245                 250                 255

Gly Ala Gly Asp Pro Leu Gly Met Pro Asn Asn Thr Gly Arg Gln Gln
                260                 265                 270

Lys Lys Lys Lys Gly Asp Gly Gln Pro Val Asn Gly Leu Cys Gln Met
            275                 280                 285

Leu Gly Lys Ile Ile Ala Gln Gln Asn Gln Ser Arg Gly Lys Gly Pro
        290                 295                 300

Gly Lys Lys Asn Lys Lys Asn Pro Glu Lys Pro His Phe Pro Leu
305                 310                 315                 320

Ala Thr Glu Asp Asp Val Arg His His Phe Thr Pro Ser Glu Arg Gln
                325                 330                 335

Leu Cys Leu Ser Ser Ile Gln Thr Ala Phe Asn Gln Gly Ala Gly Thr
            340                 345                 350

Cys Thr Leu Ser Asp Ser Gly Arg Ile Ser Tyr Ala Val Glu Phe Ser
            355                 360                 365

Leu Pro Thr His His Thr Val Arg Leu Ile Arg Val Thr Ala Ser Pro
    370                 375                 380

Ser Ala
385
```

RECOMBINANT PROTEINS FOR THE FUSION OF THE PORCINE REPRODUCTIVE AND RESPIRATORY SYNDROME VIRUS AND ITS USE IN DIAGNOSIS

FIELD OF THE INVENTION

This invention, in general, refers to recombinant proteins suitable for the diagnosis of a porcine pathogen, and in particular, to recombinant fusion proteins which comprise the protein of the nucleocapsid of the porcine reproductive and respiratory syndrome virus (PRRSV), obtained both from European isolates and from American isolates, and its use in the diagnosis of PRRSV.

BACKGROUND OF THE INVENTION

The causative agent of the porcine reproductive and respiratory syndrome (PRRS) is a new arterivirus (PRRSV) isolated for the first time in Europe [Wensvoort et al., Vet. Quarterly, 13, (1991), 121–130] and later in the United States [Collins et al., J. Vet. Diagn. Invest., 4, (1992), 117–126].

PRRSV causes an important pathology in the porcine livestock, characterised by reproductive disorders in the female pigs (miscarriages, piglets born dead or weak), and an increase of the perinatal mortality as well as dyspnea and piglet pneumonia [Terpstra et al., Vet. Quarterly, 13, (1991), 131–136].

PRRSV is an enveloped RNA virus, of approximately 62 nm of diameter, the viral genome of which comprises a single-stranded RNA of positive polarity of approximately 15 kilobases (kb) in length. The genome contains eight overlapping open reading frames (ORF) [Meulenberg et al., Virology, 192, (1993), 62–72]. The virion contains 6 structural proteins encoded by ORFs 2 to 7 [Meulenberg et al., Virology, 206, (1995), 155–163; van Nieuwstadt et al., J. Virol., 70, (1996), 4767–4772]. The ORF7 encodes the nucleocapsid protein (protein N), which is the most immunogenic protein of PRRSV [Sanz et al., Second Symposium on Aujeszky and PRRS viruses, Copenhagen, Denmark (1995)], making it a good candidate for the detection of specific antibodies to the virus, and therefore, for the diagnosis of the disease.

Two different antigenic groups of PRRSV have been described, which correspond to the American and European isolates. The Japanese PRRSV isolates, as well as other Asiatic isolates are antigenicaly related with the American isolate. A characteristic example of a European PRRSV isolate is that deposited at the ECACC under the deposit number V93070108 [Spanish Patent ES 2.074.950], whereas a representative example of an American isolate of PRRSV is that identified as VR-2332 [European Patent EP 0 529 584]. The European and American isolates of PRRSV exhibit a different genotype [Meng et al., Archives of Virology, 140 (1995), 745–755] with important antigenic differences [Wensvoort et al., J. Vet., Diagn. Inves., 4, (1992), 134–138].

The serological differences between the European and American isolates complicate the diagnosis of the disease, as in many cases there is no cross-reactivity between the respective porcine sera (perhaps due to the absence of linear immunodominant epitopes). Additionally, the recent introduction in Europe of vaccines based on the American isolate represents an additional complication in the serological analysis of infected and/or vaccinated animals. Therefore, it is necessary to develop a diagnostic method which may allow to discriminate between both isolates, both in individual and in mixed populations, with the object of performing an accurate distinction with regard to the origin of the virus.

There are kits for the detection of the presence of PRRSV or of antibodies which recognise PRRSV, specific for the European and American isolates.

The usual methods for the diagnosis of PRRSV comprise carrying out an assay based on immunoperoxidase (IPMA) or the performance of an ELISA type assay based on pig's lung alveolar macrophages or on antigenic recombinant proteins.

The techniques based on IPMA are expensive and bloody techniques, which require the use of pig's lung alveolar macrophages coming from the sacrifice of animals, being it possible that said macrophages could be contaminated or infected with other pathogens [unless gnotobiotic or specific pathogen free (SPF) animals are used], and are not susceptible to automation as they require visual inspection under the microscope.

ELISA techniques based on macrophages require the use of macrophage extracts and therefore, present the same problems, in that sense, as the techniques based on IPMA. Additionally, the use of antigen in the form of a cell extract requires an internal reference with the same cell extracts, but without infection, in case there was any serum from an animal from the field which had natural reactivity, i.e. which had natural antibodies, which could mask the result.

The ELISA techniques based upon PRRSV recombinant proteins require the production of viral antigen in appropriate amounts and in an active form. The production of PRRSV antigens, for example the nucleocapsid protein, in tissue culture, is troublesome and expensive. On the other hand, the production of PRRSV recombinant proteins using recombinant baculovirus in permissive cells poses many problems, as the expression of said proteins in that system is costly and not very efficient, the proteins expressed are insoluble and only a small soluble fraction is recovered, which is the one used in the ELISA. Likewise, the products of ORF 3, 5 and 7 of PRRSV expressed by recombinant baculovirus in insect cells are difficult to purify. Additionally, reference uninfected insect cells must be included to rule out natural reactivity.

In general, diagnostic methods must be reliable, reproducible, sensitive, simple, cost-effective, of a wide spectrum and, advantageously, shall use active antigens the production of which, in unlimited amounts, is simple and cost-effective. Additionally, in the case of pathogens which have isolates with genetic, antigenic and pathogenic differences, it is convenient that they discriminate between the different isolates.

The currently available methods used for the diagnosis of PRRSV do not satisfactorily fulfil all the characteristics which have to be demanded from a diagnostic method and, therefore, there is still a need for other methods for the diagnosis of PRRSV which solve all or some of the problems mentioned above.

The invention provides recombinant fusion proteins, which comprise the nucleocapsid protein of PRRSV obtained both from European and American isolates, of use for the diagnosis of PRRSV. The invention also provides methods and kits for the diagnosis of PRRSV which comprise the use of said recombinant fusion proteins. The nucleic acid sequences which essentially encode said recombinant fusion proteins constitute an additional object of the present invention.

DETAILED DESCRIPTION OF THE INVENTION

The recombinant fusion proteins object of this invention comprise an amino acid sequence selected among the sequences identified (see the section regarding the LIST OF SEQUENCES) as SEQ. ID. No.: 1 and SEQ. ID. No.:2, or an active fragment of the same. The term "active fragment", in the sense used in this description, refers to a protein fragment that is suitably recognised by positive sera against PRRSV, i.e. a fragment of ORF7 of PRRSV recognised in such a way that it allows the discrimination between PRRSV positive and negative sera.

SEQ. ID. No.: 1 shows the amino acid sequence corresponding to the nucleocapsid protein of a European isolate of PRRSV, specifically the one identified as Toledo 4/96 [Example 1], generally known as "European isolate" in this description, while SEQ. ID. No.: 2 shows the amino acid sequence corresponding to the nucleocapsid protein of an American isolate, specifically the one identified as Canada 14/96 (Example 2), generally known as "american isolate" in this description.

The recombinant fusion proteins also comprise an amino acid sequence, of variable length and composition, derived from the system chosen for the expression of the recombinant fusion protein, to which SEQ. ID. No.: 1, or SEQ. ID. No.: 2, or an active fragment of the same is fused, either directly, or through a binding section formed by a small number of amino acids derived from the genetic manipulation of the expression system for the recombinant fusion protein. Examples of said amino acid sequences include the full or partial gene product of gene 10 of phage T7, glutathione-S-transferase, β-galactosidase and the product of the malE gene.

In a specific embodiment of this invention, the recombinant fusion proteins comprise an amino acid sequence chosen from SEQ. ID. No.: 1 and SEQ. ID. No.: 2, or an active fragment of the same, fused to a residue of 259 amino acids originating from the protein of gene 10 of phage T7, by means of a binding section of 4–6 amino acids. In a specific and preferred embodiment of this invention, the recombinant fusion proteins have the amino acid sequences identified as SEQ. ID. NO.: 8 or SEQ. ID. No.: 9.

The recombinant fusion proteins provided by this invention can be obtained by expression of the sequence that encodes the nucleocapsid protein of PRRSV fused to the sequence that encodes another protein, or a part of it, as it happens, for example, in plasmids pET, pGEX, pEx, and pMal, which contain gene 10 of phage T7, the glutathione-S-transferase gene, the β-galactosidase gene and the malE gene, respectively, in a suitable expression system such as a prokaryote, for example a micro-organism belonging to the genus Escherichia, Bacillus, Salmonella, Listeria, Yersinia, etc.

The sequence that encodes the nucleocapsid protein of PRRSV can be obtained from the viral RNA by conventional methods which comprise, for example, the synthesis of a copy DNA (cDNA) by reverse transcription and the enzymatic amplification of the nucleic acid fragment which contains the gene of ORF7 of PRRSV by means of the polymerase chain reaction (PCR) using the suitable primers.

After this, the complete sequence that encodes the nucleocapsid protein of PRRSV is cloned into a plasmid which is used to transform appropriate host cells. Occasionally, the plasmid with the complete sequence of ORF7 of PRRSV is stabilised by cloning in a suitable cellular system, where the orientation and the size of the insert are also checked, and is subsequently cloned into the host cells suitable for the expression of the recombinant fusion protein. Any of the plasmids normally used in the transformation of prokaryotes can be employed.

The correct expression of the recombinant proteins was analysed by sodium dodecylsulphate polyacrilamide gel electrophoresis (SDS-PAGE) and Coomassie blue staining or by immunoblotting, while its antigenicity was determined by an ELISA assay.

In a specific embodiment, the complete sequence of ORF7 of PRRSV, both of the European isolate and of the American isolate, has been cloned in plasmid pET3x, stabilised in E. coli DH5 cells, from where, having checked the orientation and size, it has been extracted and cloned in E. coli BL21 cells for the expression of the corresponding recombinant fusion protein.

The recombinant fusion proteins of this invention, containing the nucleocapsid protein of either the European or the American isolate of PRRSV, have been expressed in E. coli BL21 at very high expression levels when expressed as very large sized fusion proteins [45 or 46 kilodaltons (KDa)] (see Examples 3.4.1. and 4.4.1.). Previous attempts to express the nucleocapsid protein of PRRSV without fusing to other proteins or fragments of the same, or as small fusion proteins, did not allow the production of detectable levels of said protein. Although the recombinant fusion proteins provided by this invention produce inclusion bodies, said proteins can be easily recovered by solubilisation with guanidinium chloride. The recombinant proteins of this invention, with no additional manipulation, excepting a simple dilution in phosphate buffered saline (PBS), can be used to coat a suitable solid support prior to its use for diagnostic purposes.

The expression of the nucleocapsid protein of PRRSV in the form of a recombinant fusion protein in E. coli takes place at very high levels and it can be easily purified, hence making said protein an ideal candidate for the development of methods and kits for the diagnosis if PRRSV.

The recombinant fusion proteins provided by this invention are useful as a diagnostic reagent. This hypothesis is confirmed by the fact that monoclonal antibodies that compete efficiently with PRRSV-positive sera, only recognise the complete protein (Examples 3.4.2 and 4.4.2). Additionally, the most immunodominant epitope, the one recognised by monoclonal antibodies 1CH5 and 1DH10, is a conformation dependant epitope which requires the complete sequence of the nucleocapsid protein to be recognised.

The invention also provides a method for the diagnosis of PRRSV, in particular, a method for detecting the presence of antibodies which specifically recognise PRRSV, which comprises putting into contact a biological sample from an animal with a recombinant fusion protein provided by this invention, under conditions that allow the formation of an antigen-antibody complex, and detecting the antigen-antibody complex formed. In the sense used in this description, the term "biological sample" refers to a sample coming from an animal, such as blood, serum, plasma, sputum, saliva or any other biological fluid, while the term "animal" includes all the mammals, and more specifically male pigs, female pigs and piglets.

The immunoassay can be, for instance, an indirect ELISA or a competitive ELISA. The detection of the antigen-antibody complex can be carried out by means of conventional techniques which include the production of a coloured reaction using, for example, an enzyme labelled reagent, such as peroxidase, and a suitable substrate.

Additionally, the invention provides a kit for the diagnosis of PRRSV, particularly, a kit for detecting the presence of antibodies which specifically recognise PRRSV in a biological sample from an animal, which includes a recombinant fusion protein provided by this invention and suitable means for detecting the antigen-antibody complex formed, which comprise the labelled reagent and the adequate substrate. The diagnostic kit may also contain a positive control and a negative control, with the object of facilitating the assessment of the results of the assay, by comparing against the results obtained with the standard sample.

The following examples serve to illustrate the invention, although they must not be considered as a limitation of the scope of the same.

EXAMPLE 1

Isolation of ORF7 of the European Isolate of PRRSV

The PRRSV isolate identified as Toledo 4/96, denominated "European isolate" in this description, was obtained from the serum of an animal coming from a farm situated in Toledo (Spain), in which there had been cases of miscarriages, anorexia, hyperthermia, and respiratory disorders in piglets.

The ORF7 of said isolate was obtained by means of a reverse transcription reaction (RT) followed by enzymatic amplification by the polymerase chain reaction (PCR) on the serum of the infected animal. To achieve this, 600 µl of Chaos buffer were added [to prepare 100 ml of Chaos buffer, a mixture is made with 50 g of 4.2 M guanidinium thiocyanate (GSCN), 2.5 ml of 20% sarcosyl, 1.25 ml of 2M Tris-HCl, pH: 8, 99.7 ml of water, it is filtered through a 0.22 µm filter and 0.7 moles of β-mercaptoethanol are added] to 100 µl of serum, and everything is incubated for 30 minutes at room temperature. Subsequently, 700 µl are added of a phenol: chloroform: isoamyl alcohol mixture (25:24:1), it is mixed with the aid of a vortex and centrifuged at 13.000 r.p.m. for 10 minutes at 4° C., subsequently collecting the aqueous phase (approximately 300 µl ). This phenolisation process is repeated twice. The RNA is precipitated with a 1/10 (volume) of 3 M sodium acetate pH: 5.2 and 3 volumes of absolute ethanol, it is washed with 70% ethanol and the precipitate is dried. The RNA is resuspended in 20 µl of T:E buffer (Tris:EDTA, 10:1 mM, pH: 7.5].

In order to carry out the RT-PCR, 10 µl of the suspension formed are used. To do this, 500 ng of complementary oligonucleotide primer, identified as SEQ. ID. No.: 4 are added to 10 µl of said RNA suspension, and the mixture is incubated for 10 minutes at 65° C. The mixture is then slowly allowed to cool down to room temperature. Subsequently, 2 µl of 10×Tth enzyme dilution buffer, 4 µl of deoxynucleotide triphosphates (dNTPs) [dATP, dGTP, dCTP and dTTP], oligonucleotide primers, identified as SEQ. ID. No. 3 (direct primer) and as SEQ. ID. No.: 4 (reverse primer), and 1 µl of avian myeloblastosis virus (AMB) reverse transcriptase are added and taken to a volume of 20 µl. The mixture is incubated for 1 hour at 42° C. and subsequently the reverse transcriptase is inactivated by heating at 65° C. for 5 minutes. Subsequently the mixture is taken to a final reaction mixture volume of 100 µl and 1 µl of Thermus thermophilus[Tfh] DNA polymerase (Biotools, Spain) is added. The mixture is heated at 94° C. for 3 minutes and subsequently 35 cycles are carried out, each comprising:
denaturation: 94° C. for 1 minute;
annealing: 60° C. for 1 minute; and
extension: 72 for 30 seconds,
and a final extension stage of 10 minutes at 72° C.

Operating in this manner, the fragment corresponding to the complete ORF7 [384 base pairs (bp)] of the PRRSV isolate denominated Toledo 4/96 (European isolate) was amplified.

The amplification products were detected by 1% agarose gel electrophoresis and ethidium bromide staining, and were observed under ultraviolet light (λ: 300 nm) in a Fotodyne transilluminator.

EXAMPLE 2

Isolation of ORF7 of the American PRRSV Isolate

The PRRSV isolate identified as Canada 14/96, denominated "American isolate" in this description, was obtained from the serum of an animal coming from a Canadian farm affected by PRRS.

ORF7 of said isolate was obtained by means of an RT-PCR according to the process described in Example 1, but using as oligonucleotide primer for reverse transcription the one identified as SEQ. ID. No.: 6, and as oligonucleotide primer for PCR those identified as SEQ. ID. No.: 5 (direct primer) and as SEQ. ID. No.: 6 (reverse primer). By operating in the manner indicated, the fragment corresponding to the complete ORF7 [369 base pairs (bp)] of the PRRSV isolate denominated Canada 14/96 (American isolate) was amplified and detected.

EXAMPLE 3

Expression of the Recombinant Fusion Protein that Comprises ORF7 of the European Isolate 3.1. Cloning of ORF7

The product resulting from the PCR amplification of Example 1, corresponding to the complete sequence of ORF7 of the European isolate was cloned into plasmid pMTL25 previously digested with SmaI and treated with phosphatase, with the object of providing BamHI sites compatible with the expression vectors. The resulting plasmid was denominated pPRRSE-ORF7. The plasmid DNA was sequenced according to the dideoxy nucleotide method [Sanger et al., Proc. Natl. Acad. Sci. USA, 74, (1977), 5463–5467]. The putative amino acid sequence derived from said nucleotide sequence, corresponding to the nucleocapsid protein of the European isolate of PRRSV is shown in SEQ. ID. No.: 1. The sequence analysis of the protein was performed with the PC/GENE program and PredictProtein [Rost et al., Meth. Enzymol., 266, (1996), 525–539.

Subsequently, the complete sequence encoding the nucleocapsid protein of PRRSV was subcloned into plasmid pET3x [Studier et. al., Methods Enzymol., 185, (1990), 60–89] previosly treated with phosphatase and digested with BamHI.

The pET3x plasmid containing the complete sequence of the nucleocapsid protein of PRRSV was denominated pET-PRRSVORF7E and was used to transform competent E. coli XL1 blue or DH5 cells with the object of stabilising the plasmid and verifying the orientation of the insert. The resulting colonies were screened by digestion with the appropriate restriction enzymes. In order to verify the orientation, the binding sequences of the inserts were sequenced by the dideoxy nucleotide method [Sanger et al., cited supra] using the oligonucleotide shown in SEQ. ID. No.: 7 as a primer.

3.2. Transformation of Competent E. Coli Cells for the Expression of Recombinant Proteins After checking that the orientation was correct, competent BL21 (DE3) pLysS cells [Studier et al., cited supra] were transformed with the pET-PRRSVORF7E plasmid prepared previously with the object of expressing the nucleocapsid protein of PRRSV in the form of a fusion protein with the product of gene 10 of phage T7. Agar plates with chloramphenicol and ampicillin were used to select the transformed cells.

3.3. Growth, Induction and Analysis of Transformed *E. Coli* Cells

Clones of the BL21 (DE3) pLysS *E. coli* cells containing the recombinant plasmids pET-PRRSVORF7E were grown and induced with 0.4 mM isopropylthiogalactopyranoside (IPTG) (Boehringer Mannheim, Germany) according to the method described by Martinez-Torrecuadrada et al. [Virology, 210, (1995), 391–399]. After 3 hours of induction, sufficient time to accumulate the protein without resulting in an overproduction of cells which could have lost the plasmid or were non-productive, the cells were centrifuged, washed twice with phosphate buffered saline (PBS), resuspended in a final volume of 500 µl of PBS per 20 ml of culture and were lysed by sonication [Martinez-Torrecuadrada et al., cited supra].

3.4. Analysis of the Recombinant Proteins

The correct expression of the recombinant proteins was analysed by sodium dodecysulfate polyacrilamide gel electrophoresis (SDS-PAGE) and Coomassie blue staining or by immunoblotting.

3.4.1. SDS-PAGE

One volume of loading buffer (10 mM Tris-HCl, pH: 6.9, 10% SDS, 10% mercaptoethanol, 0.02% bromophenol blue and 35% glycerol) was added to each sample and, subsequently, the samples were heated to boiling for 5 minutes before carrying out the analysis on a polyacrilamide gel with 11% SDS. The detection of the proteins was carried out by staining with Coomassie blue. A strong band is observed, that corresponds to a protein in accordance with the expected molecular weight (46 Kda) and an abundant production of the recombinant fusion protein (0.1 mg/ml). The complete sequence of the recombinant fusion protein is shown in SEQ. ID. No.: 8. The recombinant protein contains the amino acid residues derived from the product of gene 10 of T7 (amino acids 1 to 259), a binding area of 6 amino acids (amino acids 260–265) and the sequence of the complete nucleocapsid protein of the European isolate of PRRSV (amino acids 266–393).

The purification of said protein is carried out according to the methodology described by Martinez-Torrecuadrada et al. [cited supra]. The fusion protein obtained is insoluble although it can be easily solubilised with 4 M guanidinium chloride. The purity of the fusion protein obtained after the solubilisation stage is greater than 80% (determined by Coomassie blue staining).

3.4.2. Immunoblot analysis

The recombinant fusion proteins were transferred to nitrocellulose membranes using the semidry transfer technique (Bio-Rad) for 20 minutes at 22 Volts. Subsequently, the membranes were incubated for 1 hour in blocking solution (3% skimmed milk, 0.05% Tween® 20 in PBS). After blocking, the proteins were reacted with the supernatants of specific monoclonal antibodies against the nucleocapsid protein (identified as 1AC7, 1AG11, 1DA4, 1BD11, 1EB9, 1CH5 and 1DH10) [Second Symposium on Aujeszky and PRRS viruses, Copenhagen, Denmark (1995)] at 4° C. overnight. After washing twice with PBS-Tween® 20, the bound antibody was detected with peroxidase-conjugated anti-mouse IgG (Pierce) diluted 1:2000 in the blocking buffer. In order to develop the colour reaction, 4-chloro-1-naphthol (0.5 mg/ml) (SIGMA), 17% (v/v) methanol, and 0.015% hydrogen peroxide in PBS were added. The reaction was stopped by adding distilled water to the membranes. The porcine antibodies were detected using protein A labelled with peroxidase (SIGMA) following the same protocol.

The results obtained confirm that the monoclonal antibodies 1AC7, 1AG11 and 1DA4 recognise the recombinant fusion protein that contains the nucleocapsid protein of the European isolate of PRRSV by immunoblotting.

Three different reactivity patterns with the monoclonal antibodies have been observed by immunoblotting, which is indicative of the existence of three antigenic sites in the nucleocapsid protein of PRRSV. The region recognised by monoclonal antibodies 1AC7, 1AG11 and 1DA4 is well conserved between the different isolates of PRRSV. The monoclonal antibodies 1BD11 and 1EB9 reacted with the complete nucleocapsid protein and could recognise both a discontinuous epitope as well as an epitope located at the EcoNI restriction site. Finally, the monoclonal antibodies 1CH5 and 1DH10 defined another antigenic site and recognised a discontinuous epitope that requires the complete nucleocapsid.

Due to the fact that the immunoblot analysis indicated the presence of, at least, two discontinuous epitopes, the reactivity of the monoclonal antibodies was characterised by an indirect ELISA assay under conditions in which the protein was closer to its appropriate folding.

3.5. Elisa 96-well microtiter plates (LabSystem) were coated, overnight, at 4° C., with 100 µl of a 1:100 dilution of the recombinant fusion protein containing the nucleocapsid protein of the European isolate of PRRSV, expressed by *E. coli* and solubilised with 4 M guanidinium chloride in 0.05 M carbonate buffer, pH 9.6. Subsequently, the plates were incubated with the undiluted supernatants of the monoclonal antibodies or with two-fold serial dilutions of the serum of the corresponding animal for 2 hours at 37° C. After washing, the plates were incubated with the peroxidase conjugates, of anti-mouse IgG antibodies (1:1000) or protein A (1:5000) in the same buffer described above. The reaction was detected by adding 2,2'-azino-di[ethyl]-benzothiazoline [ABTS] [Sigma] as substrate, and was stopped by addition of 1% SDS. The optical density of the samples was determined at 405 nm in an ELISA reader (Bio-Tek Instruments, United States).

The results obtained by ELISA are shown in Table 1.

TABLE 1

Characterisation of monoclonal antibodies that specifically recognise the nucleocapsid protein of PRRSV

| Monoclonal Antibody | PRF-E Toledo 4/96 |
| --- | --- |
| 1CH5 | ++ |
| 1DH10 | ++ |
| 1BD11 | +++ |
| 1EB9 | +++ |
| 1DA4 | +++ |
| 1AG11 | +++ |
| 1AC7 | +++ |

++: >1.0 absorbance units (405 nm)
+++: >2.0 absorbance units (405 nm)
PRF-E: recombinant fusion protein that contains the nucleocapsid protein of the European isolate of PRRSV.

As can be seen in Table 1, all the monoclonal antibodies reacted with the recombinant fusion protein expressed by *E. coli*. This data confirms that monoclonal antibodies 1CH5 and 1DH10 recognise a discontinuous epitope and require the nucleocapsid to remain partly folded. As was expected, the remaining monoclonal antibodies yielded the same reactivity pattern as that obtained by immunoblotting, which confirms the presence of two other epitopes.

EXAMPLE 4

Expression of the Recombinant Fusion Protein that Comprises ORF7 of the American Isolate 4.1. Cloning of ORF7

Exactly the same procedure as that described in Example 3.1. was repeated, but using the product resulting from the PCR amplification of Example 2, corresponding to the complete sequence of ORF7 of the American isolate, and hence, after cloning into plasmid pMTL25, previously digested with SmaI and treated with phosphatase, the plasmid known as pPRRSC-ORF7 was obtained. The plasmid DNA was sequenced according to the dideoxy nucleotide method [Sanger et al., cited supra], while the amino acid sequence analysis of the protein was carried out with the PC/GENE and PredictProtein [Rost et al, cited supra] programs. The amino acid sequence of the nucleocapsid protein of the American isolate of PRRSV is shown in SEQ. ID. No.: 2.

Subsequently, the complete sequence encoding the nucleocapsid protein of PRRSV was subcloned in plasmid pET3x [Studier et al., Methods Enzymol., 185, (1990), 60–89] previously treated with phosphatase and digested with BamHI.

The pET3x plasmid containing the complete sequence of the nucleocapsid protein of PRRSV was denominated pET-PRRSVORFC and was used to transform competent *E. coli* XL1 blue or DH5 cells. The resulting colonies were screened by digestion with the appropriate restriction enzymes. In order to verify the orientation, the binding sequences of the inserts were sequenced by the dideoxynucleotide method [Sanger et al., cited supra] using the oligonucleotide shown in SEQ. ID. No.: 7 as a primer.

4.2. Transformation of Competent *E. Coli* Cells for the Expression of the Recombinant Protein After checking that the orientation was correct, competent BL21 (DE3) pLysS cells [Studier et al., cited supra] were transformed with the pET-PRRSVORF7C plasmid prepared previously with the object of expressing the nucleocapsid protein of PRRSV in the form of a fusion protein with the product of gene 10 of phage T7. Agar plates with chloramphenicol and ampicillin were used to select the transformed cells.

4.3. Growth, Induction and Analysis of Transformed *E. Coli* Cells

Clones of BL21 (DE3) pLysS *E. coli* cells containing the recombinant plasmids pET-PRRSVORF7C were grown and induced with 0.4 mM IPTG (Boehringer Mannheim, Germany) according to the method described by Martinez-Torrecuadrada et al. [cited supra]. After 3 hours of induction, the cells were centrifuged, washed twice with phosphate buffered saline (PBS), were resuspended in a final volume of 500 µl of PBS per 20 ml of culture and were lysed by sonication [Martinez-Torrecuadrada et al., cited supra].

4.4. Analysis of the Recombinant Proteins 4.4.1. SDS-PAGE

Following the protocol described in Example 3.4.1, a strong band was observed, corresponding to a protein in accordance with the expected molecular weight (45 KDa) and an abundant production of the recombinant fusion protein (0. 1 mg/ml). The complete sequence of the recombinant fusion protein is shown in SEQ. ID. No.: 9. The recombinant protein contains the amino acid residues derived from the product of gene 10 of T7 (amino acids 1 to 259), a binding area of 4 amino acids (amino acids 260–263) and the sequence of the complete nucleocapsid protein of the American isolate of PRRSV (amino acids 264–386).

The purification of said protein is carried out according to the methodology described by Martinez-Torrecuadrada et al. [cited supra]. The fusion protein obtained is insoluble although it can be easily solubilised with 4 M guanidinium chloride. The purity of the fusion protein obtained after the solubilisation stage is greater than 80% (determined by Coomassie blue staining).

4.4.2. Immunoblot analysis

The process disclosed in Example 3.4.2. was used, but, in this case, employing the recombinant fusion protein containing the nucleocapsid protein of the American isolate of PRRSV.

The results obtained show that the monoclonal antibodies 1AC7, 1AG11 and 1DA4, specific to the nucleocapsid protein of the European isolate of PRRSV, also recognise the recombinant fusion protein that contains the nucleocapsid protein of the American isolate of PRRSV by immunoblotting.

4.5. Elisa

The process disclosed in Example 3.5. was used, but, in this case, employing the recombinant fusion protein containing the nucleocapsid protein of the American isolate of PRRSV. The results obtained by ELISA are shown in Table 2.

TABLE 2

Characterisation of monoclonal antibodies that specifically recognise the nucleocapsid protein of PRRSV

| Monoclonal Antibody | PRF-C Canada 14/96 |
| --- | --- |
| 1CH5 | +/− |
| 1DH10 | − |
| 1BD11 | − |
| 1EB9 | − |
| 1DA4 | ++ |
| 1AG11 | ++ |
| 1AC7 | ++ |

−: <0.2 absorbance units (405 nm)
+/−: 0.2–0.4 absorbance units (405 nm)
++: >1.0 absorbance units (405 nm)
PRF-C: recombinant fusion protein that contains the nucleocapsid protein of the American isolate of PRRSV.

EXAMPLE 5

Diagnosis of PRRSV by an Indirect ELISA

The reactivity of a collection of 8 field sera originating from pigs from different geographical locations throughout Europe was analysed by means of an indirect ELISA according to the methodology described above, using the recombinant fusion proteins containing the nucleocapsid protein of either the European isolate (PRF-E) or the American isolate (PRF-C), obtained according to Examples 3 and 4 respectively, as antigens. The results obtained are shown in Table 3. As can be observed, the nucleocapsid protein of PRRSV expressed in *E. coli*, as a recombinant fusion protein was recognised by a complete collection of PRRSV positive sera determined by ELISA.

TABLE 3

Assessment of pig's sera by indirect ELISA

| Serum | Antigen used | |
|---|---|---|
| | PRF-E | PRF-C |
| Positives | | |
| 1036-9 | 1.534 | 1.348 |
| 1036-2 | 1.449 | 0.611 |
| 3 Comp | 1.898 | 0.705 |
| 12 Comp | 1.662 | 0.775 |
| 1032-68 | 1.619 | 0.518 |
| 1036-1 | 1.856 | 0.320 |
| Negatives | | |
| 1032-67 | 0.330 | 0.361 |
| PRRSC- | 0.207 | 0.366 |

[Values determined by absorbance at 405 nm]
PRF-E: recombinant fusion protein that contains the nucleocapsid protein of the European isolate of PRRSV (SEQ. ID. No.: 8).
PRF-C: recombinant fusion protein that contains the nucleocapsid protein of the American isolate of PRRSV (SEQ. ID. No.: 9).

As can be seen, a more specific and preponderant reaction is observed against PRF-E, which permits the identification of PRRSV positive animals, as well as distinguishing the origin of the viral isolate.

EXAMPLE 6

Diagnosis of PRRSV by a Competitive ELISA

As an alternative to the indirect ELISA, it is possible to carry out a competitive ELISA assay which combines the use of the recombinant antigen with the specificity of the monoclonal antibodies. In general, this assay is more specific and more sensitive.

In order to carry out the competitive ELISA, 96-well microtiter plates (LabSystem) were coated, overnight at 4° C., with 100 μl (1 μg/well) of the recombinant fusion protein that contains the nucleocapsid protein of the European isolate of PRRSV expressed in *E. coli* (Example 3) solubilised with 4 M guanidinium chloride in 0.05 M carbonate buffer, pH 9.6. Subsequently, 100 μl of the serum samples to be evaluated were added (15 samples, 6 positive and 9 negative), diluted 1/5 in PBS-0.05% Tween® 20, and were incubated for 30 minutes at 37° C. Without removing the sera, 50 μl of the peroxidase-labelled monoclonal antibody 1CH5 (1:5000) in the same buffer as described above were added, and the incubation was continued for 30 additional minutes.

The reaction was detected by adding ABTS as a substrate. The reaction was stopped by addition of 1% SDS. The optical density of the samples was determined at 405 nm on an ELISA reader (Bio-Tek Instruments, United States) The results obtained are summarised in Table 4.

TABLE 4

Assessment of field samples by competitive ELISA

| Positive Sera | $A_{405}$ | Negative Sera | $A_{405}$ |
|---|---|---|---|
| C19 | 0.492 | 1984-1996 PPA1 | 1.399 |
| C45 | 0.107 | PPA3 | 1.607 |
| C58 | 0.130 | 5 | 1.646 |
| 270 | 0.710 | 18 | 1.476 |
| 273 | 0.559 | 30 | 1.276 |
| ING-CP | 0.074 | MAT GII | 1.534 |
| | | POOL N | 1.704 |
| | | LECHON | 1.555 |
| | | ING-CN | 1.571 |

The value of the cut-off point was determined by the following formula:

$$\text{Cut-off: } CN-(CN-CP)\times 0.5$$

where CN is the absorbance value at 405 nm of the negative control, and CP is that of the positive control.

A sample is considered to be positive if the 405 nm absorbance value of said sample is below the cut-off value. Otherwise, the sample is considered to be negative.

The sera had been previously typed by means of a reference assay based on immunoperoxidase (IPMA) [WO 92/21375].

In conclusion, the results of Examples 5 and 6 demonstrate the ability of the recombinant fusion proteins provided by this invention, for the indirect diagnosis of PRRSV, by detection of antibodies against the virus.

Deposit of Micro-Organisms

The plasmid denominated pET-PRRSVORF7E, containing the nucleotide sequence that encodes the nucleocapsid protein (ORF7) of the Toledo 4/96 PRRSV isolate was deposited, on the 19$^{th}$ of December of 1996, at the Colecci ón Espanola de Cultivos Tipo (CECT) [Spanish Type Culture Collection], Burjasot, Valencia (Spain), having it been assigned the deposit number CECT 4836.

What is claimed is:

1. A recombinant fusion protein which comprises a sequence of amino acids from porcine reproductive and respiratory syndrome virus (PRRSV) selected between SEQ. ID. No.: 1 and SEQ. ID. No.: 2, and a sequence of 259 amino acids extending from amino acid residue number 1 to amino acid residue number 259 of the amino acid sequence shown in SEQ. ID. No.:8 or in SEQ. ID. No.:9.

2. A protein according to claim 1, wherein the amino acid sequence from PRRSV selected between SEQ. ID. No.: 1 and SEQ. ID. No.: 2 is fused to said amino acid sequence of 259 amino acids by means of a binding area of 4 to 6 amino acids.

3. A protein according to claim 1, which comprises a sequence of amino acids selected between SEQ. ID. No.: 8 SEQ. ID. No.: 9.

* * * * *